United States Patent
Weinberg et al.

(10) Patent No.: US 9,380,959 B2
(45) Date of Patent: Jul. 5, 2016

(54) MRI-GUIDED NANOPARTICLE CANCER THERAPY APPARATUS AND METHODOLOGY

(75) Inventors: Irving N. Weinberg, Bethesda, MD (US); Pavel Stepanov, North Potomac, MD (US)

(73) Assignee: WEINBERG MEDICAL PHYSICS LLC, Bethesda, MD (US)

( * ) Notice: Subject to any disclaimer, the term of this patent is extended or adjusted under 35 U.S.C. 154(b) by 246 days.

(21) Appl. No.: 13/586,489

(22) Filed: Aug. 15, 2012

(65) Prior Publication Data

US 2013/0046169 A1 Feb. 21, 2013

Related U.S. Application Data

(60) Provisional application No. 61/524,882, filed on Aug. 18, 2011.

(51) Int. Cl.
*A61B 5/05* (2006.01)
*A61B 5/055* (2006.01)
*A61N 2/00* (2006.01)
*A61N 2/02* (2006.01)

(52) U.S. Cl.
CPC . *A61B 5/055* (2013.01); *A61B 5/05* (2013.01); *A61N 2/004* (2013.01); *A61N 2/02* (2013.01)

(58) Field of Classification Search
CPC .......... A61B 5/05; A61B 5/055; A61N 2/004; A61N 2/02
See application file for complete search history.

(56) References Cited

U.S. PATENT DOCUMENTS

| | | | |
|---|---|---|---|
| 8,154,286 B2 | 4/2012 | Weinberg | |
| 2005/0271732 A1* | 12/2005 | Seeney et al. | 424/489 |
| 2007/0196281 A1* | 8/2007 | Jin et al. | 424/9.34 |
| 2007/0197953 A1* | 8/2007 | Slade et al. | 604/19 |
| 2009/0315560 A1* | 12/2009 | Weinberg | G01R 33/3852 324/309 |
| 2011/0068791 A1 | 3/2011 | Weinberg | |

FOREIGN PATENT DOCUMENTS

WO 2009155522 A1 12/2009

OTHER PUBLICATIONS

U.S. Appl. No. 61/385,662, filed Sep. 23, 2010; Weinberg.
Aksel et al.; Local planar gradients with order-of-magnitude strength and speed advantage; Magnetic Resonance in Medicine; 2007; pp. 134-143; vol. 58, No. 1.
Lubbe et al.; Clinical Experiences with Magnetic Drug Targeting: A Phase I Study with 4'-Epidoxorubicin in 14 Patients with Advanced Solid Tumors; Cancer Research; Oct. 15, 1996; pp. 4686-4693; vol. 56.

(Continued)

*Primary Examiner* — Ruth S Smith
(74) *Attorney, Agent, or Firm* — Barnes & Thornburg LLP

(57) ABSTRACT

An apparatus and method direct nanoparticles in a body part under imaging guidance using at least one electromagnet configured and operable to create a magnetic field gradient used to direct the nanoparticles, wherein, the magnetic field gradient used to direct the nano-particles does not substantially interfere with the use of magnetic field gradients whose purpose is to image the body part.

27 Claims, 3 Drawing Sheets

(56) References Cited

OTHER PUBLICATIONS

Mansfield et al.; Limits to neural stimulation in echo-planar imaging; Magnetic Resonance in Medicine; 1993; pp. 746-758; vol. 29, No. 6.

Weinberg et al.; Increasing the oscillation frequency of strong magnetic fields above 101 kHz significantly raises peripheral nerve excitation thresholds; Medical Physics; May 2012; pp. 2578-2583; vol. 39, No. 5.

* cited by examiner

MRI-GUIDED NANOPARTICLE CANCER THERAPY APPARATUS AND METHODOLOGY

Embodiments of apparatuses and methodologies disclosed herein formed the basis of a proposal submitted to the National Institutes of Health on Jun. 6, 2011, entitled "MRI-Guided Nanoparticle Cancer Therapy System."

CROSS-REFERENCE TO RELATED APPLICATION(S)

This application relies for priority on U.S. Provisional Patent Application Ser. No. 61/524,882, entitled "MRI-GUIDED NANOPARTICLE CANCER THERAPY APPARATUS AND METHODOLOGY, filed on Aug. 18, 2011, the entirety of which being incorporated by reference herein.

FIELD OF THE INVENTION

Disclosed embodiments are directed, generally, to cancer therapy.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

Disclosed embodiments provide an apparatus and methodologies for manipulating Magnetic NanoParticles (MNPs) in the body, preferably under imaging guidance.

BRIEF DESCRIPTION OF THE DRAWINGS

A more compete understanding of the disclosed embodiments and the utility thereof may be acquired by referring to the following description in consideration of the accompanying drawings, in which like reference numbers indicate like features, and wherein.

DETAILED DESCRIPTION

Figure 1:
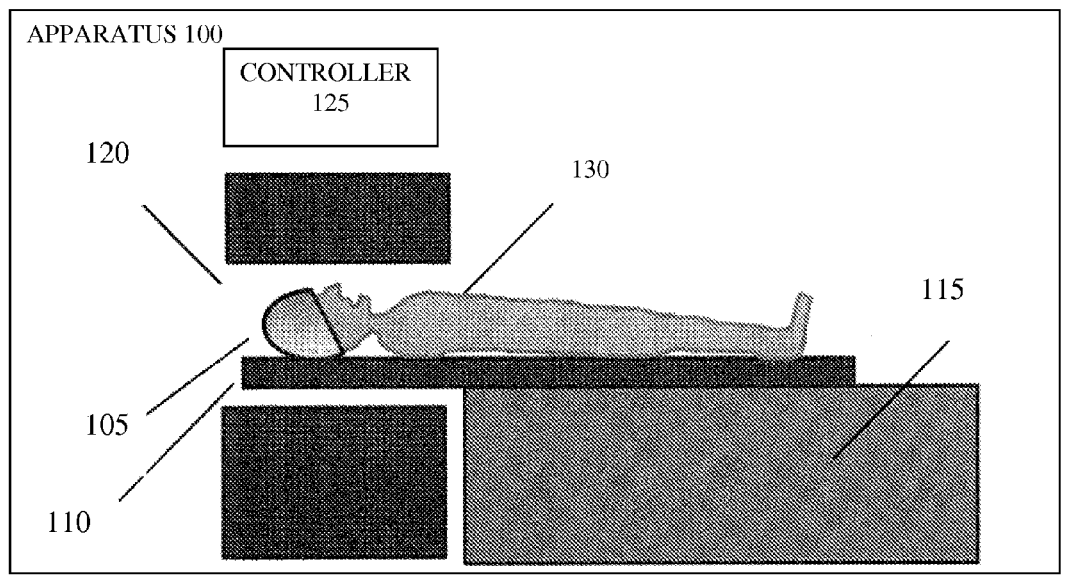
FIG. 1 an example of an embodiment of the apparatus as applied to the head, in which a cradle (upon which a patient's head rests) contains propulsive coils.

The description of specific embodiments is not intended to be limiting of the present invention. To the contrary, those skilled in the art should appreciate that there are numerous variations and equivalents that may be employed without departing from the scope of the present invention. Those equivalents and variations are intended to be encompassed by the present invention.

In the following description of various embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

Moreover, it should be understood that various connections are set forth between elements in the following description; however, these connections in general, and, unless otherwise specified, may be either direct or indirect, either permanent or transitory, and either dedicated or shared, and that this specification is not intended to be limiting in this respect.

Disclosed embodiments provide a method and apparatus for manipulating Magnetic NanoParticles (MNPs) in the body, for example, under imaging guidance.

For the purposes of this disclosure, the term "nanoparticles" includes particles smaller than 10 microns in size, which may be bound to chemicals or structures that have pharmacological or beneficial physical effects in the body under certain conditions, or which may have beneficial effects themselves under certain conditions (for example, to retard blood flow in an aneurysm). For the purposes of this disclosure, the term "magnetic nanoparticles" includes nanoparticles containing magnetizable materials, as well as materials that can be diamagnetic, or which have intrinsic magnetic properties, or which may contain coils or other electrical configurations that can generate currents or voltages upon application of magnetic fields.

An apparatus designed in accordance with the disclosed embodiments may include one or more propulsive coils or sets of coils, used in conjunction with one or more electrical current generators that create pulsed magnetic gradients. These pulsed magnetic gradients may then be used to deliver the MNPs to desired locations in the body. The use of the term "propulsive coils" in the present application is intended to include the application of the coil for the propulsion of MNPs, without necessarily limiting other applications of the coils. The propulsive coils may be toroidal, planar, or of another configuration, as desired to create appropriate magnetic gradient fields for propulsion of MNPs in specific body locations. A planar coil configuration, for example, would be useful for manipulating MNPs in superficial locations of the body like the spine. An example of a planar coil configuration (used for imaging, and not for propulsion) was presented by B. Aksel, L. Marinelli, B. D. Collick, C. Von Morze, P. A. Bottomley, and C. J. Hardy, in the article entitled "Local planar gradients with order-of-magnitude strength and speed advantage," published in 2007 by the journal Magnetic Resonance in Medicine, vol. 58, no. 1, pages 134-143.

As discussed further herein, the propulsive coil may also be used for other purposes, for example, to increase the magnetization of materials in the body or to assist in the creation of images of materials in the body. The use of the term "coil" implies at least one electromagnet or electrical configuration, that may include or be used in conjunction with magnetizable materials (for example, ferrite cores) in order to produce magnetic gradient fields.

In accordance with at least one embodiment, the one or more propulsive coils may be inserted into a Magnetic Resonance Imaging (MRI) scanning system (for example, to retrofit a conventional MRI scanning system; in such an implementation the propulsive coils and other hardware and software necessary to implement the disclosed embodiment with an MRI scanning system may be included in a kit for installation as part of such a retrofit or upgrade).

A typical MRI scanning system or scanner is a device in which the patient lies within a large, static magnet (i.e., a magnetic field that is on all of the time) where the static magnetic field is used to align the magnetization of some materials or particles in the body, and radio frequency fields are used to systematically alter the alignment of this magnetization.

In most MRI systems, the materials affected by the altered alignment are nuclear protons. In some magnetic resonance scanners, the materials affected by the altered alignment are electrons, and in other scanners the materials consist of magnetic nanoparticles. In the case where the affected materials are electrons, the MRI scanning process is often called Electron Paramagnetic Resonance Imaging (EPRI). In the case where the affected materials are electrons, the MRI scanning process is often called Magnetic Particle Imaging (MPI). The alteration in alignment causes the affected materials to produce one or more rotating magnetic fields that are detectable by the scanner. The detected rotation of the magnetic fields is recorded to construct an image of the scanned area of the body. Magnetic field gradients cause affected materials at different locations in space to rotate at different speeds. By applying magnetic field gradients in different directions, 2D images or 3D volumetric images can be obtained in many orientations.

MRI can provide good contrast between the different soft tissues of the body, which makes it especially useful in imaging the brain, muscles, the heart, and cancers. Unlike CT scans or traditional X-rays, MRI does not use ionizing radiation.

It should be understood that the propulsive coil(s) provide the ability to push MNPs from their initial positions to various locations in the body, as well as to pull the MNPs from various initial locations to other locations. Moreover, these propulsive coil(s) also provide the ability to stabilize the MNPs in their initial locations.

Prior work in manipulation of MNPs with magnetic gradients employed permanent magnets held near the body part, as taught in the article by A. S. Lübbe entitled "Clinical Experiences with Magnetic Drug Targeting: A Phase I Study with 4'-Epidoxorubicin in 14 Patients with Advanced Solid Tumors," published in the journal Cancer Research, volume 56, pages 4686-4693, on Oct. 15, 1996 (and incorporated by reference in its entirety). The use of permanent magnets in such a manner would not be possible in a typical MRI system, due to the large forces that would be applied on the permanent magnets by the MRI static field, and the interference by the permanent magnets in the magnetic gradient pulses that are used by the MRI scanner to form an image. The magnetic gradient pulses that are used by the MRI scanner typically have a maximum magnitude of 40 mT that is applied over a distance of 70 cm, which is not strong enough to move the MNPs. Applying pulsed magnetic gradients with higher magnitudes has been conventionally difficult because of the resulting nerve stimulation caused by induced magnetic fields, as discussed by P. Mansfield and P. R. Harvey in an article entitled "Limits to neural stimulation in echo-planar imaging," published in the journal Magnetic Resonance in Medicine, vol. 29, number 6, pages 746-758, in 1993.

From the above considerations, one can determine that it would be difficult if not impossible to manipulate MNPs within an MRI system using conventionally known methods. This difficulty is problematic because a physician may prefer to visualize the concentration of MNPs within the body in the course of their manipulation. Thus, the present invention addresses the challenge of manipulating MNPs under MRI guidance by utilizing pulsed magnetic gradients to propel the MNPs.

In accordance with at least one embodiment, the pulsed magnetic gradients created by the propulsive coil(s) are not contemporaneous with the pulsed magnetic gradients used by the MRI system to create an image of the body and/or MNPs in the body. For example, the propulsive magnetic gradient pulses are interleaved with the magnetic gradients used for imaging purposes, or may precede or follow the magnetic gradients used for imaging purposes. This lack of contemporaneity implies that the pulsed magnetic fields used to propel the MNPs do not interfere with the process of collecting an image with the MRI scanner, where "interference" is defined for the purposes of this description as a process that would cause reduced quality of the MRI scanner image.

In at least one alternative embodiment, strong pulsed magnetic are used to propel MNPs and also as part of the process of creating an image of the body and/or MNPs in a patient's body. Unlike the prior art, in which the magnetic gradients used to create an image are of low magnitude, at least one presently disclosed embodiment employs features disclosed in U.S. Pat. No. 8,154,286, by the present inventor, Irving Weinberg, entitled "Apparatus and method for decreasing bio-effects of magnetic fields", issued Apr. 10, 2012 (and incorporated by reference in its entirety), and published in the scientific literature in an article by I. N. Weinberg, P. Y. Stepanov, S. T. Fricke, R. Probst, M. Urdaneta, D. Warnow, H. Sanders, S. C. Glidden, A. McMillan, P. M. Starewicz, and J. P. Reilly, entitled "Increasing the oscillation frequency of strong magnetic fields above 101 kHz significantly raises peripheral nerve excitation thresholds," in a May 2012 article in the journal Medical Physics, vol. 39, no. 5, pages 2578-83 (and incorporated by reference in its entirety). By employing one or more magnetic gradient pulses with very short rise-times and/or fall-times (for example, less than 100 microseconds) as disclosed in U.S. Pat. No. 8,154,286, the magnitude of the magnetic gradients can be at least ten times higher than in the prior art (for example, 400 milliTeslas). Such high magnitudes would be similar to those previously obtained with permanent magnets for manipulating MNPs, as in the above-cited publication by Lübbe et al. Thus, the same coils used to produce propulsion can be used to create an image in the MRI scanner. As discussed above, the process of creating an image in an MRI scanner includes the alteration of rotational frequencies of materials in the body, through the application of pulsed magnetic gradients, typically by modifying the resonant frequencies of polarizable particles in a space-dependent manner. The use of propulsive coils to both propel MNPs and collect images with the MNI scanner implies that the pulsed magnetic fields used to propel the MNPs do not interfere with the process of collecting an image with the MRI scanner.

In accordance with at least one presently disclosed embodiment, a pulsed magnetic gradient may be applied by the propulsive coil(s) to materials in a patient's body in order to increase magnetization of the materials, prior to the application of other sequences of pulsed magnetic gradients. This use of a prior pulse is termed "pre-polarization", and is taught by U.S. patent application Ser. No. 12/888,580, having Irving Weinberg as an inventor and entitled, "ULTRA-FAST PRE-POLARIZING MAGNETIC RESONANCE IMAGING METHOD AND SYSTEM" (incorporated by reference in its entirety). The use of propulsive coils to both propel MNPs and increase magnetization of materials within the MRI scanner implies that the pulsed magnetic fields used to propel the MNPs do not interfere with the process of collecting an image with the MRI scanner.

The operation of the pulsed magnetic field gradients created by the propulsive coil(s) may be so rapid and strong that the overall motion of the nanoparticles is greater than if the pulsed magnetic field gradients were more gradual in their onset, just as a hammer is more able to drive a nail than a slowly-applied force.

Pulsed magnetic fields created by the propulsive coils may establish a polarization of the MNPs so that a subsequent magnetic gradient field created by the propulsive coils will exert a strong force on the polarized MNPs before the polarization has had a chance to decay.

In the configuration shown in FIG. 1, the propulsive coils 105 are configured into a cradle that holds a patient's head. The cradle may be rigidly attached to a horizontal surface 110, e.g., a patient gurney, table or bed, so that the magnetic forces due to the interaction of the MRI system and the propulsive coils do not cause motion or deformity of the cradle.

It should be understood that the propulsive coils may be inserted into the MRI system 115, as in FIG. 1, or alternatively may be built into the MRI system.

FIG. 1 shows an example of the apparatus 100, in which a cradle (upon which a patient's head rests) contains propulsive coil(s) 105. The cradle is attached to a horizontal surface 110, which can be inserted into an MRI system 115. As shown in FIG. 1, the MRI system 115 includes a bore 120. The horizontal surface 110 is supported and moved by an actuator. Additionally, included is a controller 125 that includes hardware and/or software for controlling operation of the propulsive coil(s) 105 so as to generate required propulsive forces to direct nano-particles to particular parts of a patient's body 130 while not interfering with the magnetic field gradients generated by the MRI scanner 115. Therefore, the controller 125 is coupled to and communicating with both the MRI scanner hardware and/or software and the remaining components of the apparatus 100. Furthermore, depending on the embodiment of the apparatus 100, the controller 125 may be configured to control the timing of activation of the propulsive coil(s) 105 and/or strength of magnetic field generated by those propulsive coil(s) to not interfere with the magnetic field gradient(s) generated by the MRI scanner 115 or work in cooperation with the MRI scanner 115 to generate the magnetic field gradients used for imaging.

Figure 4:
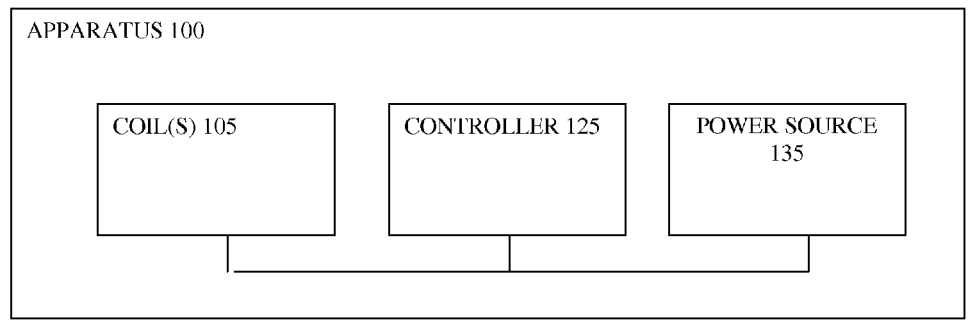
FIG. 4 illustrates additional details of the apparatus illustrated in FIG. 1.

Thus, as illustrated further in FIG. 4, the controller 125 is coupled to a power source 135 controlled by hardware and/or software for controlling operation of the propulsive coil(s) 105 so as to generate required propulsive forces to direct nano-particles to particular parts of a patient's body while not interfering with the magnetic field gradients generated by the MRI scanner 115.

Figure 2:
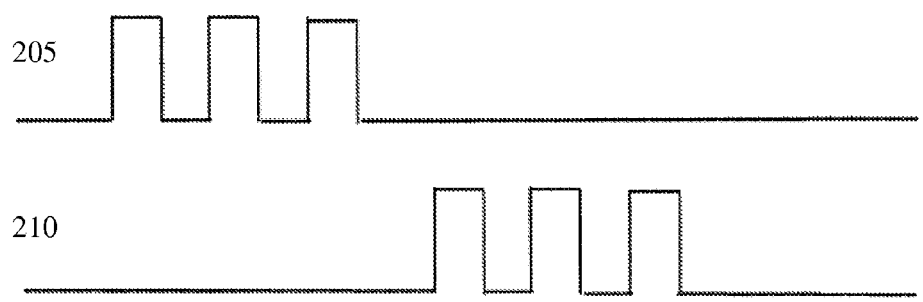
FIG. 2 shows typical operation of the disclosed embodiments.

FIG. 2 shows typical operation of the disclosed embodiments, in which a set of gradient pulses 205 are created by the MRI system 115 in order to image the patient, followed by a set of gradient pulses 210 created by the propulsion coil(s) 105 in order to direct MNPs to various locations in the patient's body.

Disclosed embodiments rely in part on prior development by the inventors, including the following (which are all incorporated by reference in their entirety):

1. APPARATUS AND METHOD FOR DECREASING BIO-EFFECTS OF MAGNETIC GRADIENT FIELD GRADIENT (WO/2009/155522, PCT/US2009/047960 and related patent applications, which describes methods of creating strong pulsed magnetic fields without causing unpleasant bio-effects in such short times as not to interfere with other magnetic gradient pulses).

WO/2009/155522 fully discloses inventive concepts that differ from the prior art by prescribing multi-phasic pulse trains within a short period of time similar to the neurological response time $t_{response}$; unlike the pulse sequences previously taught. As explained therein, the generation of magnetic field gradients (e.g., switching gradients) may elicit undesirable responses in a living organism by induction of electrical pulses in nerves and other electrically-sensitive tissues. When studying neurological tissues, the changes in magnetic field gradients depolarize nerves, once a threshold is reached. This threshold becomes higher as the pulse duration becomes shorter. The relationship between these variables follows a traditional, hyperbolic curve.

Further, as explained therein, as the laws of physics dictate, changes in magnetic fields result in the generation of electrical fields. Changes in magnetic field gradients in tissue, therefore, also result in the formation of electric fields. With respect to MRI, magnetic field gradients have at least one component of particular interest: the slew rate. The slew rate refers to the rate of change in the magnitude of the gradient, which is typically measured in Teslas per meter per second (T/m/s).

As a result of the conventional need to reduce gradient magnitude, conventional MRI diagnosis takes longer, and has reduced spatial resolution, than it would otherwise have with a higher magnetic gradient field strength. As should be immediately apparent, one impetus for increasing slew rates is to reduce scan time.

WO/2009/155522 further explains that, it is postulated that, if a given MRI sequence requires a certain number of pulses, then the application of shorter (but stronger) pulses, and of pulses with shorter ramp times, would permit the MRI sequence to be completed in a shorter time period (i.e., faster) than conventional techniques, which would save time to improve safety for unstable patients and also may reduce the cost of the MRI sequence.

The application further states that a second incentive for increasing slew rate is to increase gradient field strength, which improves spatial resolution. For a given prescribed pulse sequence, the faster one can ramp up the magnetic field per pulse, the higher the gradient strength will be for the same overall scan time. Since the gradient strength is proportional to the spatial resolution of the MRI image obtained, a higher slew rate will result in a better spatial resolution. Increased spatial resolution may improve medical diagnosis in some cases.

Conventionally, limits have been set for slew rates for MRI imaging based on studies concerning the presence of bio-effects due to neuronal stimulation. These limits have placed a limit on currently-available scanning technologies. However, the conventional generation of a magnetic field gradient with a very small duration presents technological challenges as well. Accordingly, there also has been a technological barrier to decreasing the duration of the magnetic field gradient pulses.

With respect to technological limitations, in some MRI devices, switches are used to trigger the generation of a magnetic field gradient. The types of switches traditionally used include Insulated-Gate Bipolar Transistor ("IGBT") and Metal Oxide Semiconductor Field Effect Transistor ("MOSFET")-based devices. However, these traditional switches are not capable of creating magnetic filed gradients with a sufficiently short duration to avoid neuronal stimulation.

Recent developments in switches offer a solution to the technological problem experienced with prior art MRI devices. Specifically, several generations of plasma physics experimentalists have led the development of reliable solid-state switches and pulse-forming lines that are just now being introduced into the community. (See H. Sanders and S. Glidden, "High Power Solid State Switch Module," in International Power Modulator Symposium Conference Record, pp. 563-566, 2004).

Those high-power solid-state switches are capable of triggering pulses of ten-thousand amps in one microsecond, orders of magnitude higher than the IGBT and MOSFET-based systems currently employed in commercial gradient field generators for MRI systems (See D. A. Seeber, J. H. Hoftiezer, and CH. Pennington, "Pulsed current gradient power supply for microcoil magnetic resonance imaging," in Magnetic Resonance Engineering, 15(3): 189-200, 2002).

Thus, as disclosed in WO/2009/155522, magnetic field gradients with a magnitude greater than that traditionally employed may be applied. In one embodiment, the gradient may be up to five (5) times greater than previously applied. In other embodiments, the magnitude may be greater.

Additionally, bio-effects from magnetic field gradients are decreased by applying a magnetic field gradient to tissue within a time frame below the response threshold for that tissue. Thus, one can take advantage of magnetic pulse delivery systems that are more powerful than traditional systems used to deliver MRI pulses.

Figure 3:
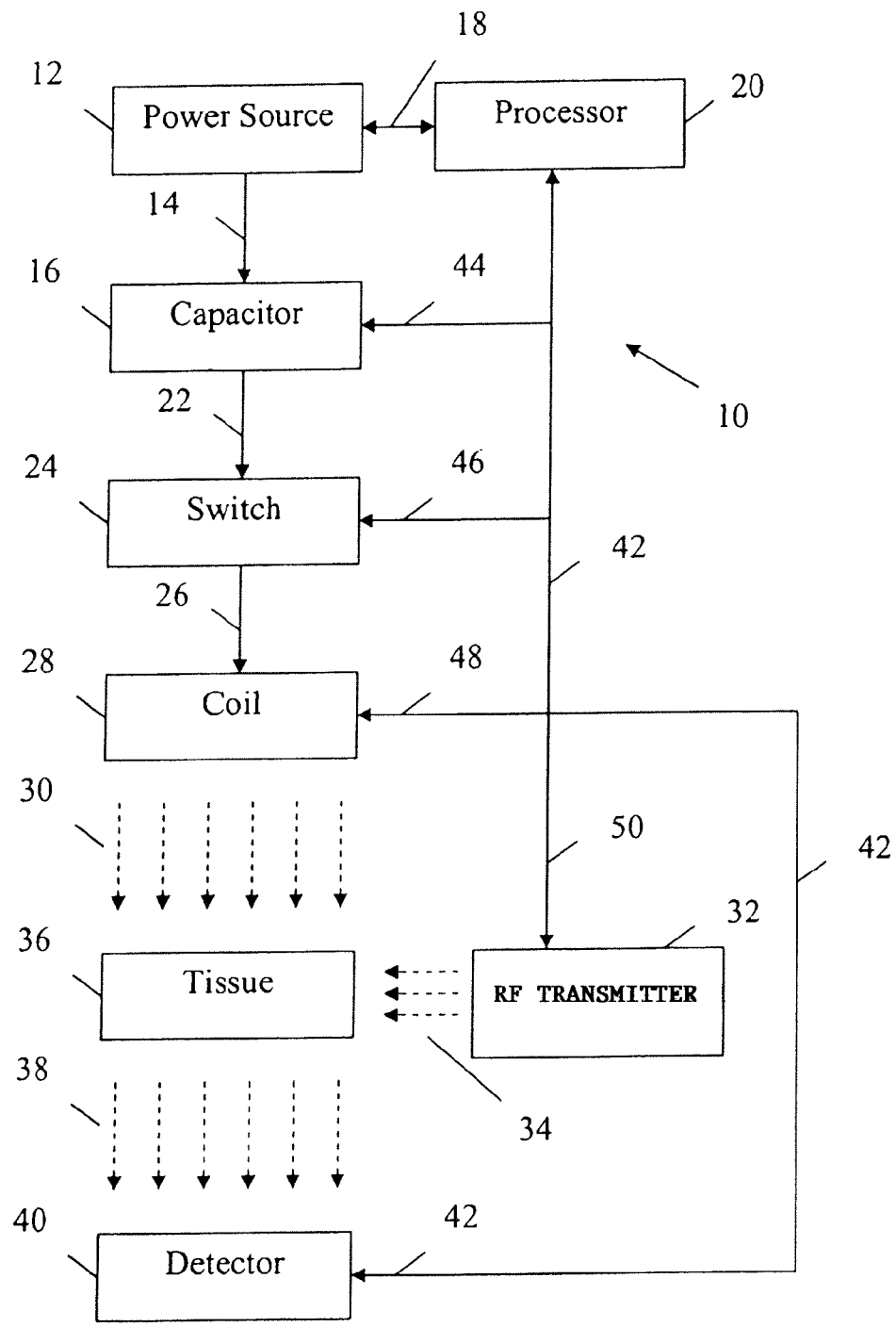
FIG. 3 is identical to FIG. 1 of WO/2009/155522, entirety of which having been incorporated by reference.

As explained with reference to FIG. 3 (which is identical to FIG. 1 of WO/2009/155522, incorporated herein by reference in its entirety), the MRI device 10 relies upon a plurality of capacitors 16 employed to generate successive magnetic field gradients. In the second flow path, power from a power source 12 is provided to a processor 20, which may be of any type suitable for executing instructions, generating data, receiving data, storing data, and the like. Accordingly, when the capacitors 16 discharge the stored charge, the stored charge passes through a communication line 22 to a switch 24, connected, via a communication line 26, to a coil(s) 28. Accordingly, when the capacitor 16 is discharged, energy from the capacitor 16 is passed to the coil(s) 28, which generates a magnetic field 30.

Thus, as further explained in WO/2009/155522, a magnetic field gradient with a minimum amplitude of 1 milliTesla per meter (mT/m) may be generated and maintained for at least about 1 microsecond and up to about 10 milliseconds (this is the plateau time period, as discussed below); the magnetic field gradient may be changed in a time frame small enough to fail to solicit a response from neurological tissue. WO/2009/155522 further disclosed that application of the magnetic field gradient with rise- and fall-times of less than about 10 microseconds will establish suitable conditions to avoid triggering a biological response from neurological tissue.

Further, WO/2009/155522 disclosed use of a rise time or fall time of 10 microseconds or less. The slew rate is also increased as a result of the reduced pulse ramp times. Thus, the plateau magnitude is increased, as compared to the prior art, because of several factors including the plateau magnitude being increased because of improved switching techniques and because the tissues are depolarized and repolarized within a short period of time.

Thus, WO/2009/155522 disclosed that the magnitude of the pulse during the time period $t_{plateau}$ may be any value. As discussed above, the magnitude may be as small as 1 mT/m but may be smaller or greater than 1 mT/m, as required or desired for a particular application. While the magnitude of the magnetic field is theoretically unbounded at its upper limit, it is foreseeable that the magnitude may be 1000 mT/m or less.

As noted above, 10 microseconds is a sufficiently short time period in which to change a magnetic field so that tissue does not react biologically. Naturally, the shorter the duration of the rise or fall times, the smaller the likelihood of eliciting a biological response. In keeping with this premise, one or both of the rise and fall times may be less than about 9 microseconds, less than about 8 microseconds, less than about 7 microseconds, less than about 6 microseconds, less than about 5 microseconds, less than about 4 microseconds, less about than 3 microseconds, less than about 2 microseconds, or less than about 1 microsecond and need not be identical in duration.

2. FLEXIBLE METHODS OF FABRICATING ELECTROMAGNETS (U.S. Patent Application No. 61/385,662 and related patent applications, which facilitates the creation of propulsion coils having adequate cooling and/or high-frequency current-handling properties to deliver magnetic gradient fields of sufficient strength to propel nanoparticles).

3. ULTRA-FAST PRE-POLARIZING MAGNETIC RESONANCE IMAGING METHOD AND SYSTEM (application Ser. No. 12/888,580 and related patent applications, which specifies a method and apparatus for applying a pulsed magnetic field in order to pre-polarize a specimen).

While this invention has been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

Additionally, it should be understood that the functionality described in connection with various described components of various invention embodiments may be combined or separated from one another in such a way that the architecture of the invention is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

As a result, it will be apparent for those skilled in the art that the illustrative embodiments described are only examples and that various modifications can be made within the scope of the invention as defined in the appended claims.

What is claimed is:
1. An apparatus comprising:
a power source;
at least one coil coupled to the power source; and
a controller coupled to the power source and the at least one coil and configured to control the power source and the at least one coil to apply a first magnetic field to at least one magnetizable particle to orient the at least one magnetizable particle along a direction of the first magnetic field,
wherein the controller is configured to control the power source and the at least one coil to subsequently apply a subsequent magnetic field for a time duration in a direc- tion that opposes a previous magnetic orientation of the at least one magnetizable particle, wherein the time duration is less than both the magnetic relaxation and rotation times of the at least one magnetizable particle so that the at least one magnetizable particle is translated in motion by a force due to interaction of the subsequent oppositional magnetic field with the previously oriented at least one magnetizable particle.

2. The apparatus of claim 1, further comprising an imaging system configured to image a body part using one or more magnetic field gradients, wherein the controller controls the power source and the at least one coil to produce at least one magnetic field gradient to direct the at least one magnetizable particle, and wherein the at least one magnetic field gradient used to direct the at least one magnetizable particle is not contemporaneous with the one or more magnetic field gradients generated by the imaging system.

3. The apparatus of claim 2, wherein the at least one magnetic field gradient used to direct the at least one magnetizable particle is a pulsed magnetic field.

4. The apparatus of claim 2, wherein the imaging system is a Magnetic Resonance Imaging (MRI) scanning system.

5. The apparatus of claim 2, wherein the at least one magnetic field gradient produced to direct the at least one magnetizable particle has a transition time of less than 100 microseconds.

6. The apparatus of claim 1, wherein the controller controls the power source and the at least one coil to direct the at least one magnetizable particle, and wherein the at least one magnetizable particle is smaller than 10 microns in size.

7. The apparatus of claim 1, wherein the controller controls the power source and the at least one coil to produce at least one magnetic field gradient to direct the at least one magnetizable particle, and wherein the at least one magnetizable particle is bound to chemicals or structures that have pharmacological or beneficial physical effects in a body under certain conditions.

8. The apparatus of claim 1, wherein the controller controls the power source and the at least one coil to produce at least one magnetic field gradient to direct the at least one magnetizable particle, and wherein the at least one magnetizable particle has pharmacological or beneficial physical effects in a body under certain conditions.

9. The apparatus of claim 1, further comprising an imaging system configured to image a body part using one or more magnetic field gradients, wherein the controller controls the power source and the at least one coil to produce at least one magnetic field gradient for producing propulsive forces to direct the at least one magnetizable particle so that the at least one magnetic field gradient used to direct the at least one magnetizable particle is controlled by the controller to be active at different times than the one or more magnetic field gradients used by the imaging system to form images.

10. The apparatus of claim 1, wherein the controller controls the power source and the at least one coil to produce at least one magnetic field gradient that pushes or pulls the at least one magnetizable particle from an initial position to other locations in a body part.

11. The apparatus of claim 1, wherein the controller controls the power source and the at least one coil to produce at least one magnetic field gradient that stabilizes the at least one magnetizable particle in a specific location.

12. The apparatus of claim 1, further comprising an imaging system configured to image a body part using one or more magnetic field gradients, wherein the controller controls the power source and the at least one coil to produce at least one magnetic field gradient to produce propulsive forces to direct the at least one magnetizable particle, and wherein the produced at least one magnetic field gradient assists in image formation for the imaging system to image the at least one magnetizable particle by modifying a resonant frequency of the at least one magnetizable particle in a space-dependent manner.

13. The apparatus of claim 1, wherein the at least one coil is in a planar configuration.

14. The apparatus of claim 1, wherein the controller controls the power source and the at least one coil to provide at least one magnetic field gradient to produce propulsive forces to direct the at least one magnetizable particle, wherein the at least one magnetic field gradient has a slew rate selected such that the at least one magnetic field gradient does not cause nerve stimulation in a body part.

15. A method for propelling at least one magnetizable particle by applying magnetic fields, the method comprising:

creating a first magnetic field using a power source coupled to at least one coil under the control of a controller; and creating a subsequent magnetic field using the power source coupled to the at least one coil under the control of the controller, wherein the first magnetic field orients the at least one magnetizable particle along a direction of the first magnetic field, and wherein the subsequent magnetic field orients the at least one particle in a direction that opposes the previous magnetic orientation of the particle caused by the first magnetic field, wherein the subsequent magnetic field is applied to the at least one magnetizable particle for a time duration that is less than both the magnetic relaxation and rotation times of the at least one magnetizable particle so that the at least one magnetizable particle is translated in motion by a force due to interaction of the subsequent oppositional magnetic field with the previously-oriented at least one magnetizable particle.

16. The method of claim 15, further comprising generating one or more magnetic field gradients using an imaging system to image a body part, wherein at least one magnetic field gradient is generated under the control of the controller to direct the at least one magnetizable particle, and wherein the at least one magnetic field gradient generated to direct the at least one magnetizable particle is not contemporaneous with the one or more magnetic field gradients generated by the imaging system.

17. The method of claim 16, wherein the imaging system is a Magnetic Resonance Imaging (MRI) scanning system.

18. The method of claim 15, wherein the controller controls the power source and the at least one coil to direct the at least one magnetizable particle, wherein the at least one magnetizable particle is smaller than 10 microns in size.

19. The method of claim 15, wherein the controller controls the power source and the at least one coil to direct the at least one magnetizable particle, wherein the at least one magnetizable particle is bound to chemicals or structures that have pharmacological or beneficial physical effects in a body under certain conditions.

20. The method of claim 15, wherein the controller controls the power source and the at least one coil to direct the at least one magnetizable particle, wherein the at least one magnetizable particle has pharmacological or beneficial physical effects in a body under certain conditions.

21. The method of claim 15, wherein at least one magnetic field gradient is used to produce propulsive forces to direct the at least one magnetizable particle, and the magnetic field gradient is a pulsed magnetic field gradient.

22. The method of claim 15, further comprising generating one or more magnetic field gradients using an imaging system to image a body part,
wherein the controller controls the at least one power source to power the at least one coil to create at least one magnetic field gradient to direct the at least one magnetizable particle at different times than magnetic field gradients generated by the imaging system to form images.

23. The method of claim 15, wherein the at least one coil produces at least one magnetic field gradient to push or pull the at least one magnetizable particle from an initial position to other location in a body part.

24. The method of claim 15, wherein the at least one coil produces at least one magnetic field gradient to stabilize the at least one magnetizable particle in a specific location.

25. The method of claim 15, wherein at least one magnetic field gradient is created by the at least one coil to produce propulsive forces to direct the at least one magnetizable particle, wherein the at least one magnetic field gradient created to direct the at least one magnetizable particle has a transition time of less than 100 microseconds.

26. The method of claim 15, further comprising generating at least one magnetic field gradient by the at least one coil to produce propulsive forces to direct the at least one magnetizable particle and generating one or more magnetic field gradients using an imaging system to image a body part,
wherein the at least one magnetic field gradient generated by the at least one coil assists in image formation for the imaging system to image the at least one magnetizable particle by modifying a resonant frequency of the at least one magnetizable particle in a space-dependent manner.

27. The method of claim 15, wherein at least one magnetic field gradient is created by the at least one coil and used to produce propulsive forces to direct the at least one magnetizable particle, wherein the at least one magnetic field gradient has a slew rate selected such that the at least one magnetic field gradient does not cause nerve stimulation in the body part.

* * * * *